United States Patent [19]

Cox et al.

[11] Patent Number: 4,758,225
[45] Date of Patent: Jul. 19, 1988

[54] DEVICES FOR SAMPLING, DRAINAGE OR INFUSION OF LIQUIDS FROM OR TO THE HUMAN OR ANIMAL BODY

[75] Inventors: Jeffrey A. Cox, Keighley; Liakatali G. H. Parapia, Leeds, both of United Kingdom

[73] Assignee: Pharmacia Limited, Milton, United Kingdom

[21] Appl. No.: 928,883

[22] Filed: Nov. 7, 1986

[30] Foreign Application Priority Data

Nov. 8, 1985 [GB] United Kingdom ................ 8527646

[51] Int. Cl.$^4$ ............................................. A61M 5/00
[52] U.S. Cl. ..................................... 604/126; 604/167; 604/168
[58] Field of Search ............... 604/122, 126, 164–170, 604/256; 128/764–766

[56] References Cited

U.S. PATENT DOCUMENTS

| | | | |
|---|---|---|---|
| 4,106,491 | 8/1978 | Guerra | 604/167 |
| 4,200,096 | 4/1980 | Charvin | 604/168 X |
| 4,531,937 | 7/1985 | Yates | 604/122 X |
| 4,626,245 | 12/1986 | Weinstein | 604/167 |
| 4,689,047 | 8/1987 | Bauer | 604/122 |

FOREIGN PATENT DOCUMENTS

| | | |
|---|---|---|
| 0014403 | 8/1980 | European Pat. Off. . |
| 0056103 | 1/1981 | European Pat. Off. . |
| 0197180 | 4/1985 | European Pat. Off. . |
| 33392.2 | 12/1980 | Fed. Rep. of Germany . |
| 1277377 | 6/1972 | United Kingdom . |
| 1297794 | 11/1972 | United Kingdom . |
| 2000976 | 1/1979 | United Kingdom . |
| 2006035 | 5/1979 | United Kingdom . |

Primary Examiner—Dalton L. Truluck
Attorney, Agent, or Firm—Fitch, Even, Tabin & Flannery

[57] ABSTRACT

A device for use in the sampling or infusion of liquids from or to the human or animal body, comprising a chamber for receiving fluid, a cannula in communication with the chamber, at least one valve means operable in an open condition to connect the chamber with a source or drain of liquid and in a closed condition to seal the chamber therefrom, and chamber venting means allowing the escape of air from the chamber while preventing the escape of liquid therefrom.

10 Claims, 2 Drawing Sheets

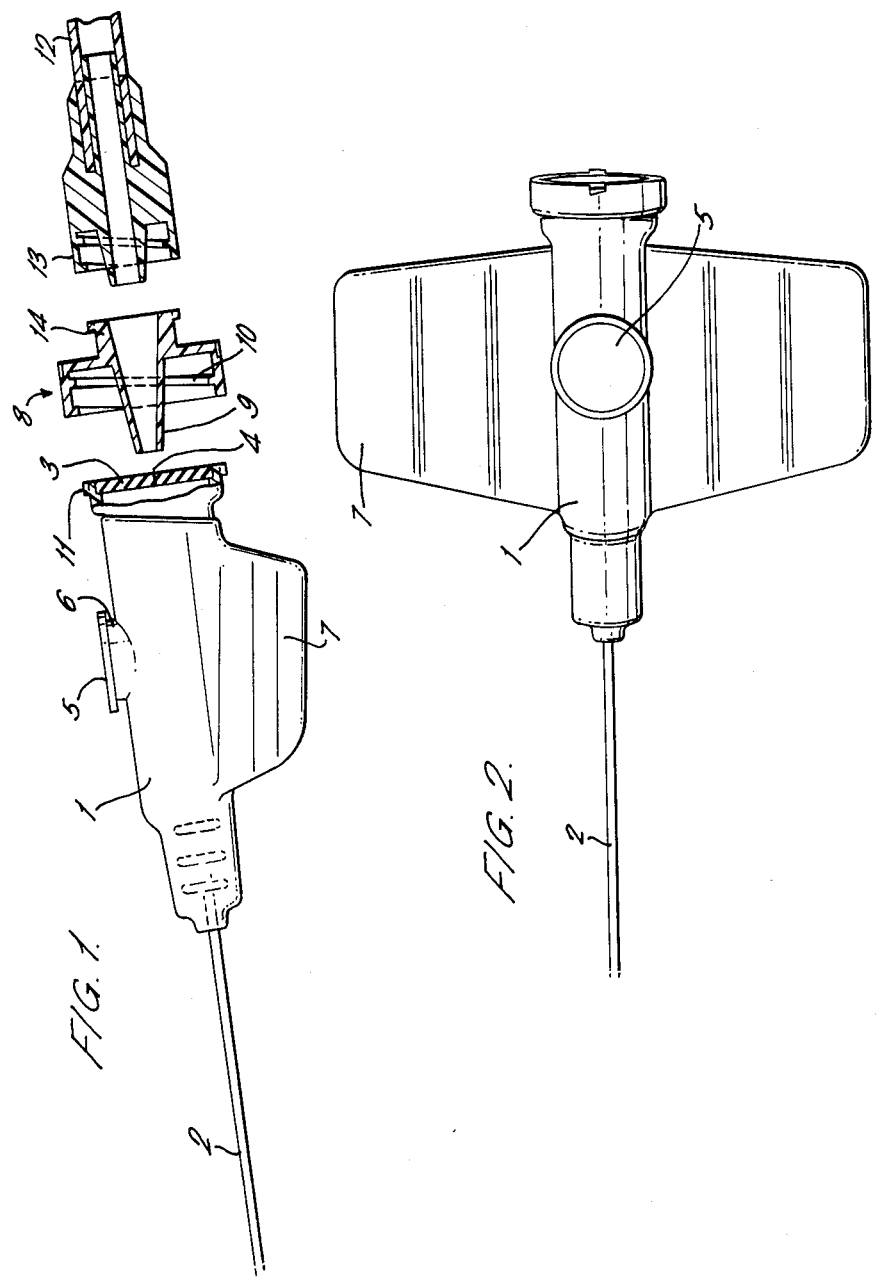

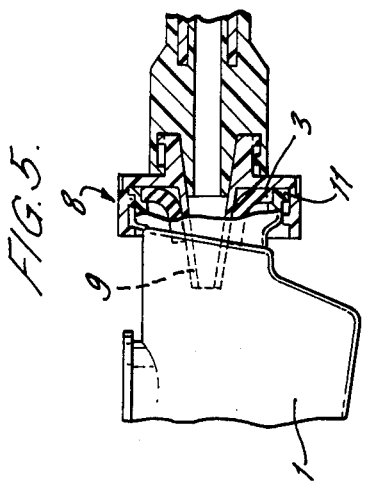
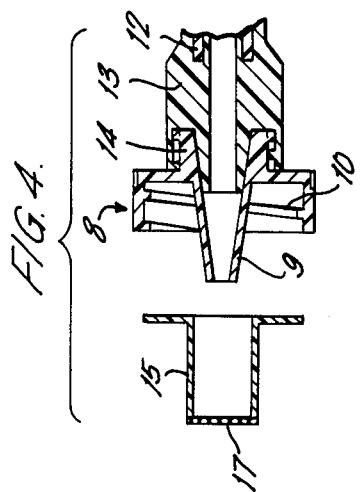
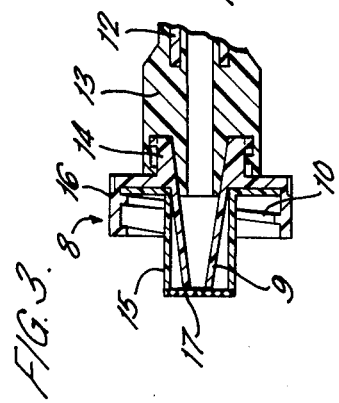
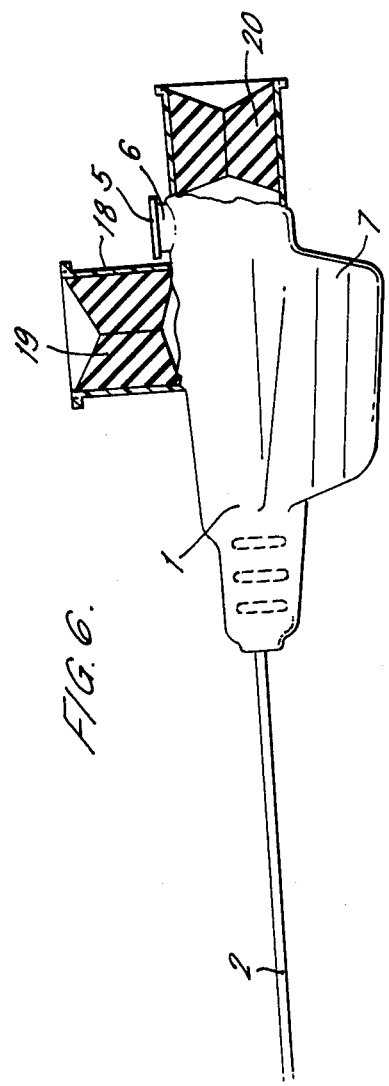

DEVICES FOR SAMPLING, DRAINAGE OR INFUSION OF LIQUIDS FROM OR TO THE HUMAN OR ANIMAL BODY

BACKGROUND OF THE INVENTION

This invention relates to the sampling, drainage or infusion of liquids from or to the human or animal body and in particular but not exclusively to a device for use in intravenous sampling or infusion via a cannula and to an adapter for use in connecting the device to a catheter.

It is known for a cannula to be used in sampling or infusion of liquids in a device in which the cannula communicates with a chamber having one or more ports through which a needle or catheter may pass into the cannula. In such devices liquid may be sampled or infused by connection to a drain or a source of liquid, respectively by means of a catheter. It has hitherto been a problem with such devices that an airlock may develop in the chamber or in the catheter. A further problem is that liquid may be lost during coupling of the device to catheters and the like and that under certain circumstances the loss of liquid may be hazardous, for example, when sampling blood from the body of an infective patient or when supplying potentially irritant medication with associated hazards to the patient and operator.

SUMMARY OF THE INVENTION

According to the present invention there is disclosed a device for use in the sampling or infusion of liquids from or to the human or animal body comprising a chamber for receiving fluid, a cannula communicating with the chamber, at least one valve means operable in an open condition to connect the chamber with a source or drain of liquid and in a closed condition to seal the chamber therefrom, and chamber venting means allowing the escape of air from the chamber while preventing the escape of liquid therefrom.

Preferably the venting means is a hydrophobic filter comprising an air-permeable barrier of a hydrophobic material. Preferably this material is polytetrafluoroethylene having a pore size in the range of 0.2 to 0.5 microns.

Advantageously the valve means is disposed in a position and orientation permitting an elongate member such as an introducing needle or a probe catheter penetrating the valve means to extend linearly through the chamber and the cannula. An advantage of such an arrangement is that an introducing needle may be inserted through the chamber and the cannula into the body so that the cannula may then be introduced into the body, or alternatively a probe catheter may be passed through the chamber and through the already introduced cannula so as to extend into the body.

Advantageously the cannula communicates with one end of the chamber, a first valve means is disposed at the other end of the chamber for admitting an elongate member and a second valve means is disposed at an intermediate position in a side port of the chamber. An advantage of such an arrangement is that a second means of injecting or sampling liquid is provided through the second valve means.

Preferably the cannula communicates with one end of the chamber while the venting means is disposed at or adjacent the other end of the chamber so that in use the venting means is disposed as far away as possible from the body and releases air from the uppermost portion of the chamber. An advantage of such an arrangement is that the venting means is then optimally located for eliminating air locks.

The valve means in such a device may conveniently comprise an elastomeric membrane having a central puncture, which membrane may be penetrated at the puncture site by a cooperating ducted member to provide a flow path through the membrane in an open condition of the valve means and which is self sealing on withdrawal of the member in a closed condition of the valve means.

The term puncture here is used to indicate that the membrane has been pierced, for example, by a needle so that in the absence of any deforming forces the elastomeric qualities of the membrane effect a self sealing action.

Preferably such a membrane has an outer surface with respect to the chamber lying substantially flush with the surrounding outer surface of the device. Such an arrangement avoids the accumulation of matter which might serve as a bacteria trap.

Preferably the device includes means for fastening the cooperating member to the device in the open condition of the valve means so that the cooperating member is supported and secured to the device. Conveniently the fastening means is a threaded fastener which has the added advantage of providing a controlled penetrating force to the member during connection.

Preferably the membrane is of an uncured rubber material such as gumstock.

Alternatively the membrane may be of silicone rubber.

According to a further aspect of the invention there is disclosed an adapter for use with the device comprising a cooperating ducted member having a distal end for use in penetrating the membrane at the puncture site and means for connection of a proximal end of the ducted member to a catheter. The term "catheter" in this context is intended to include the tubing of a giving set or drainage set, or a syringe which may, for example, have a LUER connector, or any other type of tube used in the sampling, drainage or infusion of liquids.

Such an adaptor is particularly advantageous where a flush fitting membrane is used in the device and where conventional catheter connectors are to be employed so that conveniently the adapter may include a LUER connector.

Advantageously the ducted member in such an adapter is sealable at its distal end to prevent loss of liquid while not connected to the device and includes duct venting means allowing the escape of air from the ducted member while preventing the escape of liquid therefrom. This is useful when, for example, the adapter is connected to an infusion prior to being connected to the device.

Preferably the adapter includes a detachable cap having a hydrophobic filter. Conveniently the cap is threadably engageable with the adaptor.

BRIEF DESCRIPTION OF THE DRAWINGS

Particular embodiments of the invention will now be described by way of example only and with reference to the accompanying drawings of which:

FIG. 1 is a part-sectioned elevation of a device according to the present invention having a membrane valve and showing an adapter and a LUER connector prior to assembly;

FIG. 2 is a plan view of the device of FIG. 1;

FIG. 3 is a sectioned view of the adapter of FIG. 1 having a cap in a sealing position;

FIG. 4 is a similar view of the adapter of FIG. 3 and showing a cap prior to sealing;

FIG. 5 shows the adapter of FIG. 3 connected with the device of FIG. 1; and

FIG. 6 shows an alternative device having two valve means of the silicone rubber type.

DETAIL DESCRIPTION OF THE PREFERRED EMBODIMENT

The device of FIG. 1 has a chamber (1) and a cannula (2). A valve means comprising a membrane (3) is disposed opposite to and in line with the cannula (2) and has a central puncture (4). The membrane material is an uncured natural rubber and in this example is W-1028 gum having a thickness of 1/16 inch (0.159 cm).

Venting means comprising a chamber filter (5) obturates a side port (6) of the chamber and comprises a polytetrafluoroethylene barrier having a pore size of 0.2 microns.

Wings (7) extend on either side of the chamber for ease of attachment of the device to a body (not shown), for example, by means of adhesive tape.

An adapter (8) includes a ducted member (9) which is tapered to facilitate penetration through the membrane (3) at the puncture site (4). The adapter is fitted to the device by a threaded fastener comprising female threads (10) on the adapter which engage male lugs (11) on the device so that during threaded engagement the ducted member is progressively urged through the membrane.

A catheter (12) having a female LUER connector 13 may be connected to the adaptor (8) by engaging the male LUER connector (14).

The adapter (8) is provided with a detachable cap (15) as shown in FIGS. 3 and 4, so that in the sealing arrangement shown in FIG. 3 the cap is sealed to the adapter by a threaded connector 16. The cap (15) includes a hydrophobic cap filter (17) comprising a barrier of polytetrafluoroethylene having a pore size of 0.2 microns.

In FIG. 5 the adapter (8) without the cap (15) is shown connected to the device such that the ducted member (9) extends through the membrane (3) thereby creating a flow path communicating with the chamber.

FIG. 6 shows an alternative device having an additional side port (18) accommodating a silicone rubber valve (19). In this embodiment the valve means (20) opposing the cannula is also of silicone rubber.

The device and the adapter (8) as shown in FIGS. 1 to 5 may, for example, be used in connecting an intravenous infusion to a human patient by inserting the cannula into the patient and connecting the adapter to a catheter comprising the tubing of a giving set. The cannula may be of the steel needle type in which case cannulation can be by direct injection or the cannula may be of a plastics material in which case cannulation requires the use of an introducing needle which is initially inserted through the membrane (3) at the puncture site (4) so as to extend through the cannula (2) and may then be withdrawn after cannulation.

The chamber (1) serves as a flashback chamber during cannulation so that preferably the chamber is of a transparent plastics material so that the chamber may be observed to be filling with blood. During flashback air is expelled through the chamber filter (5) which prevents loss of blood by virtue of its hydrophobic properties. The pore size of the filter (5) is selected to be of the order of 0.2 microns which prevents the ingress of bacteria, and the material of the filter is chosen to be non-toxic and non-reactive with the chamber contents, for example polytetrafluoroethylene.

For the purpose of volume fluid infusion, before connecting the adapter (8) to the device it is first necessary to prime the tubing (12) of the giving set and the adapter with the infusion liquid and this may be carried out by connecting adapter to the tubing using the male and female LUER connectors (14 and 13) and with the cap (15) fitted to the adapter. Liquid from the giving set is then admitted to the tubing and fills both the tubing and adapter completely, with air being expelled through the filter (17). The use of a hydrophobic filter (17) in the cap (15) ensures that no liquid is lost during the priming operation and the use of a filter of polytetrafluoroethylene having a pore size of 0.2 microns ensures that the liquid is not contaminated by bacteria.

To connect the primed adapter and tubing to the device, the tubing (12) which is of a soft plastics material is clamped adjacent to the adapter (8) and the cap (15) is then removed. No loss of liquid will occur at this stage provided the tubing (12) is adequately clamped to prevent any flow of liquid. The cap may then be discarded and preferably is regarded as being a disposable item.

The adapter (8) is then fitted to the device by urging the ducted member (9) through the puncture (4) of the membrane (3) and screwing the adapter in place by means of the threaded fasteners (10 and 11). The tubing may then be unclamped to release the flow of liquid and in this condition, as show in FIG. 5, the flow path is established from the tubing through the adapter and into the chamber for delivery to the patient via the cannula. The giving set may be disconnected from the patient by clamping the tubing and unscrewing the adapter from the device to withdraw the ducted member (9) so that the membrane (3) relaxes to its closed position as shown in FIG. 1.

The setting up of a giving set for an intravenous infusion may therefore be a controlled and closed procedure using the device and adapter of the present invention. Furthermore it is envisaged that each new giving set may be supplied with a disposable adapter including a cap.

Additional medication may be injected to the chamber (1) where an additional port (18) is provided as shown in FIG. 6.

The device and adapter in accordance with the present invention is particularly advantageous where a patient requires self treatment involving infusion, as in the case of patients suffering from hemophilia and other blood disorders. The self-sealing nature of the membrane valve (3) allows the attachment of a syringe to a cannula to be a simple one-hand operation. The device also has application in chemotherapy, dialysis and anesthesia. The inclusion of the hydrophobic filter reduces the risk of air embolism or infection and enables flashback to be safely controlled without blood spillage. The device may also be used in the taking of blood samples and is particularly advantageous in obtaining samples from patients suspected of having infectious diseases where it is essential to minimize the risk of blood spillage.

While membrane type valves have been shown in the preferred embodiments, other types of valves may be used in the device, such as flap valves or ball valves and may be actuated either by a cooperating member or by fluid pressure.

Other arrangements are envisaged in which no adapter is required to connect the device to a catheter, for example, where the valve means is incorporated in a LUER connector and is actuated when engaged with a mating connector of the catheter.

A device in accordance with the present invention may be used not only for intravenous infusion and sampling but in cannulating any body cavity for infusion or drainage and may include specialized adaptions of the cannula portion of the device for such use.

It is also envisaged that a filter as disclosed above may be used in a cap attachable to the tubing of a giving set to generally avoid spillage during priming. This would avoid the present disadvantage whereby a quantity of liquid is generally lost when preparing to connect the giving set to any apparatus in order to remove air from the system. Such a filter could be supplied in a disposable cap which would allow air to be vented during priming, the tubing of the giving set then being clamped and the cap discarded.

We claim:

1. A device for use in both the sampling and infusion of liquids from or to the human or animal body comprising:
    a housing defining a chamber, a cannula connection portion, an access port, and an air venting port for releasing air in the chamber, said cannula connection portion, said access port and said air venting port each communicating with the chamber and each spaced apart from one another;
    a cannula connected to the cannula connection portion;
    means for connecting the access port to a source or drain of liquid;
    a two-way valve located in the access port for selectively opening or closing a liquid flow path extending into and out of the chamber between the access port and the cannula connection portions thereof; and
    a filter located in the air venting port, permeable to air and impermeable to both body fluids and infusion liquids so as to release air in the chamber as liquid flows along said liquid flow path.

2. A device according to claim 1 wherein said filter is a hydrophobic filter comprising an air-permeable barrier of a hydrophobic material.

3. A device according to claim 2 wherein said hydrophobic material is polytetrafluoroethylene having a pore size in the range of 0.2 to 0.5 microns.

4. A device according to claim 1 wherein the said two-way valve is disposed in a position and orientation to permit an elongate member penetrating said two-way valve to extend linearly through said chamber and said cannula.

5. A device according to claim 4 wherein the said cannula communicates with one end of the said chamber, the said two-way valve is disposed at the opposite end of the said chamber and a second valve is disposed at an intermediate position in a side port of the chamber.

6. A device according to claim 5 wherein the said cannula communicates with one end of the said chamber and the said filter is disposed at or adjacent to the opposite end of the said chamber so that, in use, the said venting means is disposed as far away as possible from the body and so that, in use, the said filter releases air from the uppermost portion of the said chamber.

7. A device according to claim 1 wherein the two-way valve consists of an elastomeric membrane defining a central puncture, which membrane may be penetrated at the puncture site by a cooperating ducted member to provide said liquid flow path through the membrane in an open condition of the said two-way valve and which is self-sealing on withdrawal of the said ducted member in a closed condition of the said two-way valve.

8. A device according to claim 7 further including means for fastening the said cooperating ducted member to the device in the open condition of the two-way valve.

9. A device according to claim 7 wherein the membrane is made from a material selected from an uncured rubber material and silicone rubber.

10. A device as claimed in claim 1 in combination with an adapter comprising a cooperating ducted member having a distal end and a proximal end, the distal end being adapted to penetrate the membrane at the puncture site, and the proximal end having means for the connection of the ducted member to a catheter.

* * * * *